(12) United States Patent
Tamaki et al.

(10) Patent No.: US 10,653,882 B2
(45) Date of Patent: May 19, 2020

(54) ELECTRICAL STIMULUS DEVICE

(71) Applicant: H2L Inc., Tokyo (JP)

(72) Inventors: Emi Tamaki, Tokyo (JP); Kenichiro Iwasaki, Tokyo (JP)

(73) Assignee: H2L Inc., Tokyo (JP)

( * ) Notice: Subject to any disclaimer, the term of this patent is extended or adjusted under 35 U.S.C. 154(b) by 0 days.

(21) Appl. No.: 16/071,778

(22) PCT Filed: Jan. 27, 2017

(86) PCT No.: PCT/JP2017/002904
§ 371 (c)(1),
(2) Date: Jul. 20, 2018

(87) PCT Pub. No.: WO2017/131145
PCT Pub. Date: Aug. 3, 2017

(65) Prior Publication Data
US 2019/0022373 A1 Jan. 24, 2019

(30) Foreign Application Priority Data
Jan. 27, 2016 (JP) .................. 2016-013040

(51) Int. Cl.
*A61N 1/04* (2006.01)
*A61B 5/11* (2006.01)
(Continued)

(52) U.S. Cl.
CPC .............. *A61N 1/0476* (2013.01); *A61B 5/11* (2013.01); *A61N 1/36014* (2013.01);
(Continued)

(58) Field of Classification Search
CPC .. A61N 1/0476; A61N 1/0452; A61N 1/0484; A61N 1/36003
See application file for complete search history.

(56) References Cited

U.S. PATENT DOCUMENTS 5,330,516 A 7/1994 Nathan
5,562,707 A 10/1996 Prochazka et al.
(Continued)

FOREIGN PATENT DOCUMENTS

JP 2001054507 A2 2/2001
JP 2013103121 A2 5/2013
(Continued)

OTHER PUBLICATIONS

International Search Report (ISR) dated Mar. 14, 2017 filed in PCT/JP2017/002904.
(Continued)

*Primary Examiner* — Alyssa M Alter
(74) *Attorney, Agent, or Firm* — Rankin, Hill & Clark LLP

(57) ABSTRACT

Provided is an electrical stimulus device including a member to be wound around an arm of a user, multiple electrodes arranged on one surface of the member, and multiple optical distance sensors arranged on the one surface of the member. An electrical stimulus signal output from an electrical stimulus generation circuit is provided to the user from a specific electrode of the multiple electrodes to provide a stimulus to a muscle of the arm at a position facing the specific electrode, and the multiple optical distance sensors detect displacement of muscles of the arm. Some electrodes of the multiple electrodes are substantially rectangular electrodes inclined with respect to a circumferential direction of the arm of the user at a predetermined angle of lower than 90°.

11 Claims, 11 Drawing Sheets

(51) Int. Cl.
  *A61N 1/36* (2006.01)
  *A61B 5/00* (2006.01)
  *A61N 1/08* (2006.01)
(52) U.S. Cl.
  CPC ..... *A61B 5/6824* (2013.01); *A61B 2562/0209* (2013.01); *A61N 1/0408* (2013.01); *A61N 1/08* (2013.01); *A61N 1/36* (2013.01); *A61N 1/36003* (2013.01)

(56) References Cited

U.S. PATENT DOCUMENTS

| | | | |
|---|---|---|---|
| 9,402,997 B1* | 8/2016 | Kosierkiewicz | A61B 5/4029 |
| 2006/0253167 A1* | 11/2006 | Kurtz | A61B 5/04001 607/48 |
| 2009/0171418 A1 | 7/2009 | Sarif et al. | |
| 2012/0059298 A1 | 3/2012 | Hoffman et al. | |
| 2015/0173640 A1 | 6/2015 | Chappell et al. | |

FOREIGN PATENT DOCUMENTS

| | | |
|---|---|---|
| JP | 2014104241 | 6/2014 |
| JP | 2015107281 A2 | 6/2015 |

OTHER PUBLICATIONS

Decision to Grant a Patent dated Nov. 7, 2017 for the corresponding Japanese Patent Application No. 2016-013040.
Extended European Search Report (EESR) dated Aug. 30, 2019 for the corresponding EP patent application No. 17744375.1.

* cited by examiner

ELECTRICAL STIMULUS DEVICE

TECHNICAL FIELD

The present invention relates to an electrical stimulus device configured to provide, to a muscle of a person's arm, an electrical stimulus signal output from an electrical stimulus signal generation circuit and detect displacement of the muscle of the arm by a sensor.

BACKGROUND ART

Typically, an attempt has been made such that multiple electrodes are attached to a person's (user's) forearm and provide electrical stimulus signals to muscles of the forearm to move a user's finger or hand according to a command from the outside. For example, it has been considered that hand/finger rehabilitation, training, motion support, etc. are performed according to the command from the outside. Moreover, it has been proposed that when the virtual reality processing of providing a video of a virtual space to a user is performed using, e.g., a head mount display, a hand and fingers are moved according to the video of the virtual space by the command from the outside to enhance reality.

The inventors of the present application have proposed an electrical stimulus device as described earlier in Patent Literature 1. The electrical stimulus device proposed in Patent Literature 1 is configured such that multiple electrodes are attached to a band to be attached to a user's forearm to provide an electrical stimulus to a muscle of the forearm.

CITATION LIST

Patent Literature

PATENT LITERATURE 1: JP-A-2014-104241

SUMMARY OF THE INVENTION

Problems to be Solved by the Invention

A user wearing the electrical stimulus device proposed in Patent Literature 1 moves one's finger or hand according to a command from the outside to the muscle of the forearm. For example, forearm muscles for moving five fingers by stimulation are known in advance, and the electrodes attached to the electrical stimulus device stimulate a specific muscle to move a finger corresponding to such a muscle.

A situation where the user wears, on the forearm thereof, a band-shaped electrical stimulus device is assumed herein. In this case, the band-shaped electrical stimulus device includes multiple electrodes, but it is necessary to sense a correspondence between the electrode and the muscle. For such sensing, when the user wears the band-shaped electrical stimulus device, a calibration process needs to be first performed to output an electrical stimulus signal from each electrode, thereby checking, in advance, which finger is moved.

Specifically, the thickness of the person's arm greatly varies depending on an individual difference in an age, a gender, a body weight, etc. Thus, when the user wears the band-shaped electrical stimulus device, it is difficult to determine, without the calibration process, a muscle facing each electrode arranged at the electrical stimulus device. Thus, the calibration process has a significantly important meaning.

However, the calibration process is the process of sequentially supplying electrical stimulus signals to many electrodes to check which one of five fingers is moved, leading to a problem that great effort and time are required.

The present invention has been made in view of these points, and is intended to provide an electrical stimulus device configured so that each arranged electrode can properly stimulate a target muscle even with an individual difference in an arm thickness or a muscle position.

Solution to the Problems

The electrical stimulus device of the present invention includes a member to be wound around an arm of a user, multiple electrodes arranged on one surface of the member, and multiple optical distance sensors arranged on the one surface of the member.

An electrical stimulus signal output from an electrical stimulus generation circuit is provided to the user from a specific electrode of the multiple electrodes to provide a stimulus to a muscle of the arm at a position facing the specific electrode, and the multiple optical distance sensors detect displacement of muscles of the arm.

At least one electrode of the multiple electrodes is a substantially rectangular electrode arranged with the substantially rectangular electrode being inclined with respect to a circumferential direction of the arm of the user at a predetermined angle of lower than 90°.

According to the present invention, the inclined substantially rectangular electrodes are arranged on the member to be wound around the arm of the user. Thus, even with a difference in the arm thickness or the arm muscle position of the user to which the electrical stimulus device is to be attached, the substantially rectangular electrodes are arranged at positions overlapping with target muscles. Thus, for the electrodes arranged in an inclined state, no calibration process is necessary, or a simple calibration process is merely performed. Accordingly, a burden in the calibration process can be reduced.

Moreover, the optical distance sensors configured to detect displacement of the muscles are arranged at the electrical stimulus device. Thus, motion of the muscle when the electrical stimulus signal is provided from the electrode of the electrical stimulus device can be directly detected by the optical distance sensor. Consequently, the electrical stimulus signal can be provided to the electrode while motion of the muscle is being monitored.

DESCRIPTION OF THE EMBODIMENTS

Hereinafter, the present invention will be described with reference to an embodiment (hereinafter referred to as a "present embodiment").

[1. Configuration of Electrical Stimulus Device]

Figure 1:
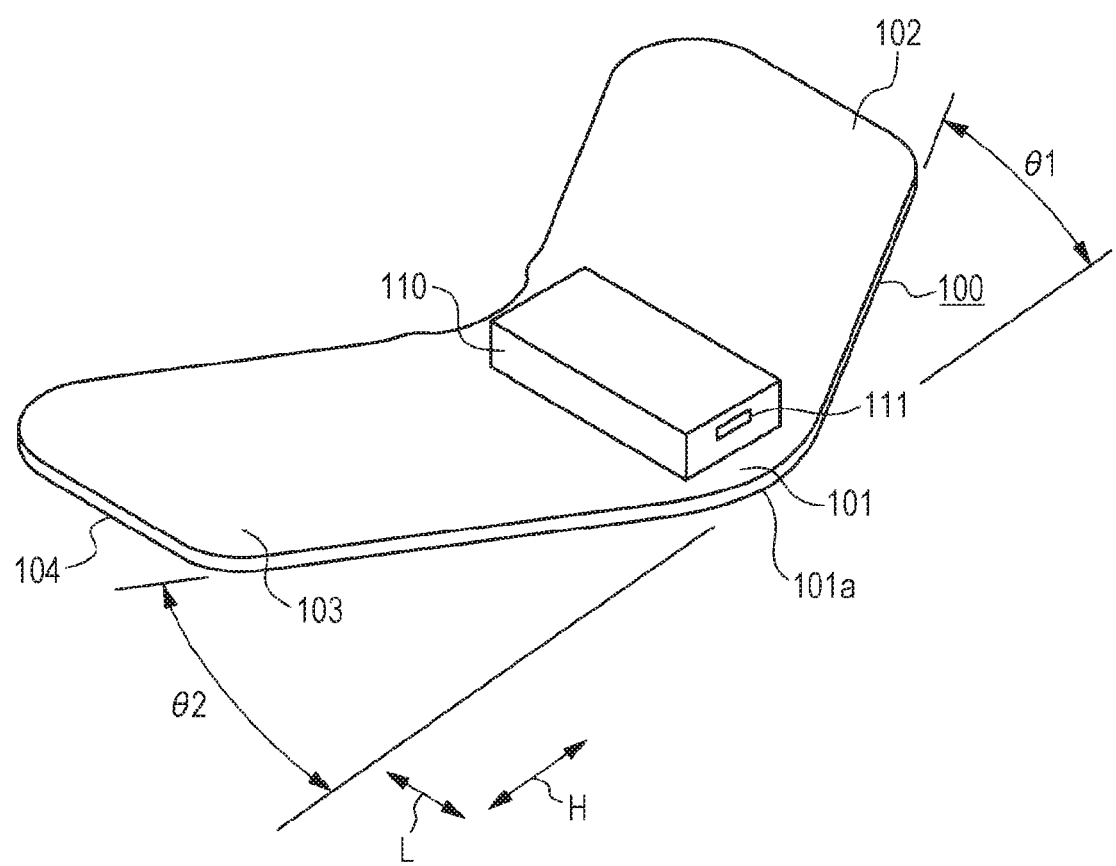
FIG. 1 is a perspective view of an electrical stimulus device of an embodiment of the present invention.

FIG. 1 is a perspective view of an electrical stimulus device of the present embodiment diagonally from above.

The electrical stimulus device of the present embodiment includes a substantially V-shaped sheet-shaped member 100. The sheet-shaped member 100 includes a resin sheet exhibiting flexibility, and a circuit housing box 110 is attached to a surface of a center portion 101 of the sheet-shaped member 100. A later-described arithmetic processing unit 150 (see FIG. 4), a battery, etc. are embedded in the circuit housing box 110. A surface (a lower surface in FIG. 1) of the sheet-shaped member 100 opposite to the surface attached to the circuit housing box 110 forms an electrode arrangement surface 104.

As will be described in an attachment example of FIGS. 3A and 3B described later, the electrical stimulus device including the sheet-shaped member 100 is attached to a user with the electrode arrangement surface 104 being wound around the forearm.

As illustrated in FIG. 1, the sheet-shaped member 100 is in the substantially V-shape, and therefore, a left portion 102 is, at a predetermined angle θ1, inclined with respect to a direction (an H-direction in FIG. 1: the H-direction curves along the arm upon attachment) as a circumferential direction of the forearm upon attachment. Similarly, a right portion 103 is, at a predetermined angle θ2, inclined with respect to the direction as the circumferential direction of the forearm upon attachment. These inclination angles θ1, θ2 as described herein are 32°. Moreover, in description below, a direction (a direction as a longitudinal direction of the arm upon attachment) perpendicular to the H-direction corresponding to the circumferential direction of the forearm will be referred to as an "L-direction."

Figure 2:
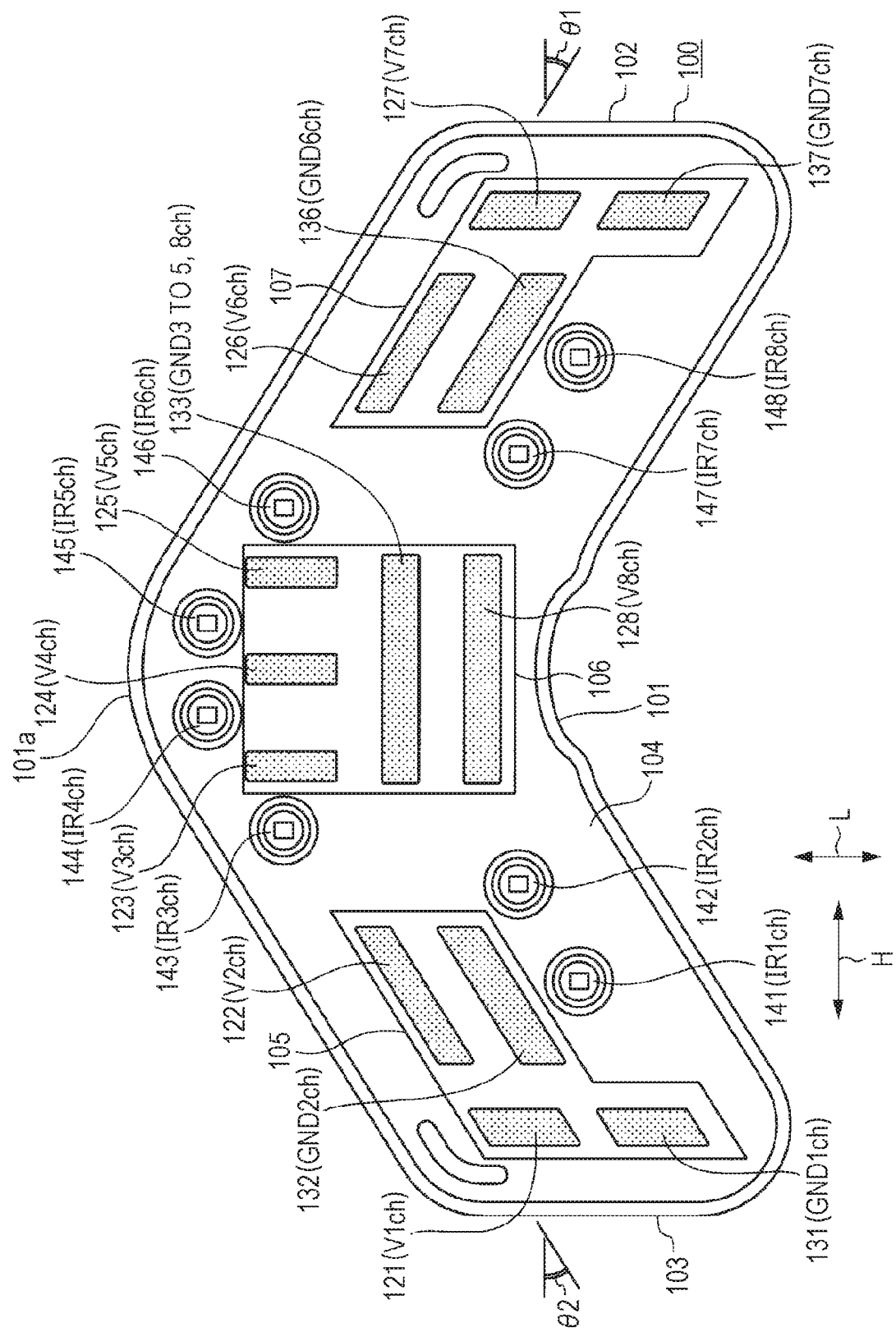
FIG. 2 is a plan view of a configuration example of an electrode arrangement surface of the electrical stimulus device of an embodiment of the present invention.

FIG. 2 is a plan view of a configuration example of the electrode arrangement surface 104.

The electrode arrangement surface 104 includes electrodes 121 to 128 configured to provide electrical stimulus signals to muscles of the forearm of the user, and ground electrodes 131 to 133, 136, 137 each paired with the electrodes 121 to 128 upon use. Note that some ground electrodes are shared upon use, and therefore, the number of electrodes 121 to 128 and the number of ground electrodes 131 to 133, 136, 137 are not necessarily coincident with each other.

Moreover, the electrode arrangement surface 104 includes optical distance sensors 141 to 148 configured to detect motion of the muscles of the forearm of the user.

A right portion electrode arrangement spot 105 is prepared at the right portion 103 (on the left side in the figure) of the electrode arrangement surface 104, and four electrodes 121, 122, 131, 132 are arranged at the right portion electrode arrangement spot 105. Of four electrodes 121, 122, 131, 132, the electrode 121 is an electrode for a channel 1 (V1ch), and the electrode 122 is an electrode for a channel 2 (V2ch). Moreover, the electrode 131 is an electrode for a ground channel 1 (GND1ch), and the electrode 132 is an electrode for a ground channel 2 (GND2ch).

The electrode 121 for V1ch and the electrode 131 for GND1ch are electrodes paired with each other upon use to provide stimuli to the muscles of the forearm, and are arranged adjacent to each other in the longitudinal direction L of the arm upon attachment.

The electrode 122 for V2ch and the electrode 132 for GND2ch are also electrodes paired with each other upon use to provide stimuli to the muscles of the forearm, and are substantially rectangular electrodes arranged with these electrodes being inclined with respect to the circumferential direction H at the same angle θ2 as the inclination angle θ2 of the right portion 103. The electrode 122 for V2ch and the electrode 132 for GND2ch are arranged adjacent to each other in the longitudinal direction L of the arm.

A center portion electrode arrangement spot 106 is prepared at the center portion 101 of the electrode arrangement surface 104, and five electrodes 123, 124, 125, 128, 133 are arranged at the center portion electrode arrangement spot 106. Of five electrodes 123, 124, 125, 128, 133, the electrode 123 is an electrode for a channel 3 (V3ch), the electrode 124 is an electrode for a channel 4 (V4ch), and the electrode 125 is an electrode for a channel 5 (V5ch). These three electrodes 123, 124, 125 for V3ch, V4ch, V5ch extend in the longitudinal direction of the arm, and are arranged substantially in parallel with each other in the circumferential direction of the arm. Moreover, the electrode 128 is an electrode for a channel 8 (V8ch). The electrode 128 for V8ch is an electrode elongated in the circumferential direction of the arm. The electrode 133 is an electrode commonly used for ground channels 3, 4, 5, 8 (GND3, 4, 5, 8ch).

The electrode 123 for V3ch, the electrode 124 for V4ch, and the electrode 125 for V5ch are electrodes configured to separately provide stimuli to different muscles of the forearm according to a channel, and the electrode 133 is commonly used as a ground electrode. Three electrodes 123, 124, 125 for V3ch to V5ch are arranged in the circumferential direction H of the arm, and the common ground electrode 133 arranged adjacent to three electrodes 123, 124, 125 in the longitudinal direction L is a rectangular electrode elongated in the circumferential direction H of the arm.

The electrode 128 for V8ch is a rectangular electrode elongated, adjacent to the ground electrode 133, in the circumferential direction H of the arm. The ground electrode 133 is also used as the ground potential of the electrode 128 for V8ch. Note that V8ch is a channel used as backup. The electrode 128 for V8ch is elongated in the circumferential direction H of the arm, and therefore, stimuli can be simultaneously provided to multiple muscles of the arm.

A left portion electrode arrangement spot 107 is prepared at the left portion 102 (on the right side in FIG. 2) of the electrode arrangement surface 104, and four electrodes 126, 127, 136, 137 are arranged at the left portion electrode arrangement spot 107. Of four electrodes 126, 127, 136, 137, the electrode 126 is an electrode for a channel 6 (V6ch), and the electrode 127 is an electrode for a channel 7 (V7ch). Moreover, the electrode 136 is an electrode for a ground channel 6 (GND6ch), and the electrode 137 is an electrode for a ground channel 7 (GND7ch).

The electrode 126 for V6ch and the electrode 136 for GND6ch are paired with each other upon use to provide stimuli to the muscles of the forearm, and are substantially rectangular electrodes arranged with these electrodes being inclined with respect to the circumferential direction H at the same angle θ1 as the inclination angle θ1 of the left portion 102. The electrode 127 for V7ch and the electrode 137 for GND7ch are arranged adjacent to each other in the longitudinal direction L of the arm.

The optical distance sensors 141, 142 are arranged at two spots in the vicinity of the right portion electrode arrangement spot 105 (on the left side in FIG. 2) of the electrode arrangement surface 104, the optical distance sensors 143, 144, 145, 146 are arranged at four spots in the vicinity of the center portion electrode arrangement spot 106 of the center portion of the electrode arrangement surface 104, and the optical distance sensors 147, 148 are arranged at two spots in the vicinity of the left portion electrode arrangement spot 107 of the electrode arrangement surface 104. These eight optical distance sensors 141 to 148 are sensors for eight channels IR1ch to IR8ch.

Each of the optical distance sensors 141 to 148 for eight channels IR1ch to IR8ch includes an infrared light emission element 141a to 148a and an infrared light receiving element 141b to 148b (see FIG. 4), and is configured to detect a change in a distance from a sensor arrangement surface to a surface of the muscle of the arm.

Note that a resin material (not shown) exhibiting adhesion is arranged at other spots of the electrode arrangement surface 104 than the electrode arrangement spots 105, 106, 107, and the adhesion of the resin material allows attachment of the electrode arrangement surface 104 with the electrode arrangement surface 104 being wound around the forearm.

Examples of the muscle to be stimulated by the electrode 121 to 128, 131 to 137 for each channel and the muscle to be detected by the optical distance sensor 141 to 148 will be described later (see FIGS. 5 and 6).

[2. Attachment Example of Electrical Stimulus Device]

Figure 3A:
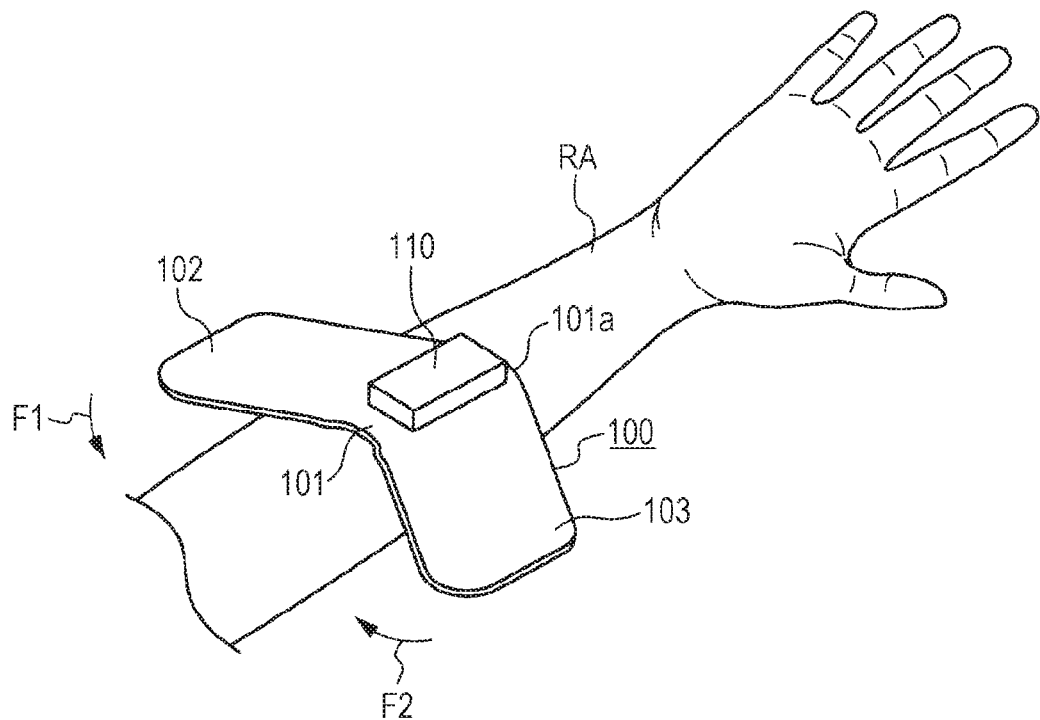
FIGS. 3A and 3B are views for describing an example of attachment of the electrical stimulus device of an embodiment of the present invention to a forearm.
Figure 3B:
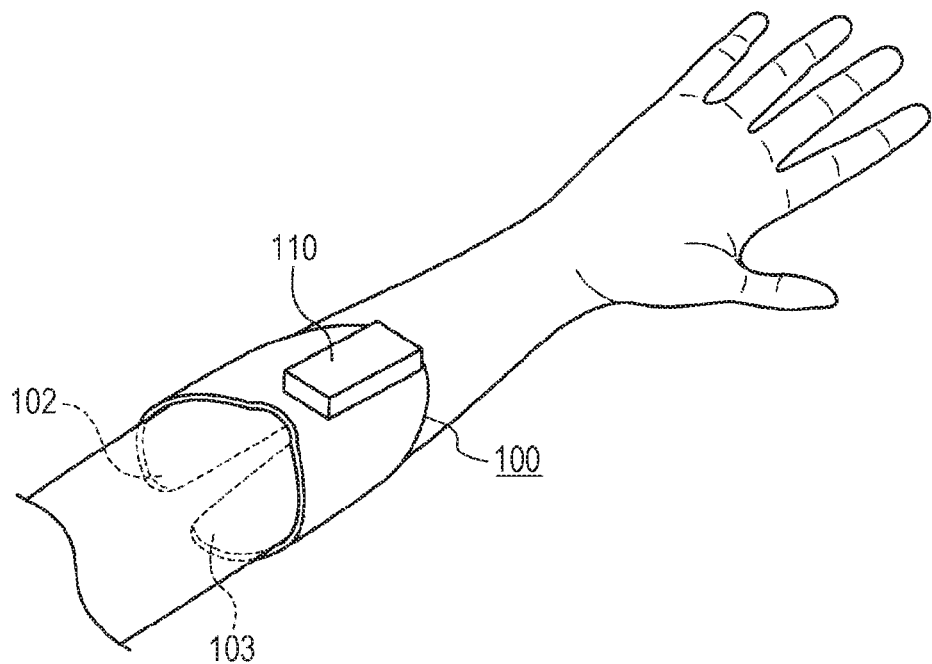

FIGS. 3A and 3B illustrate an example where the electrical stimulus device of the present embodiment is attached to the forearm.

As illustrated in FIG. 3A, the center portion 101 of the electrode arrangement surface 104 (FIG. 2) of the sheet-shaped member 100 is in contact with a spot close to the wrist of the forearm RA of the right arm of the user. In this state, the palm is at such a position that the palm faces up as illustrated in FIG. 3A. Moreover, a position relationship is brought, in which the left portion 102 is on the left side of the palm and the right portion 103 is on the right side of the palm. That is, an upper side 101a of the center portion 101 of the sheet-shaped member 100 in the substantially V-shape faces a palm side.

The user performs the process of winding the left portion 102 of the sheet-shaped member 100 around the wrist as indicated by an arrow F1 and winding the right portion 103 of the sheet-shaped member 100 around the wrist as indicated by an arrow F2.

In this manner, the electrical stimulus device is attached with the electrical stimulus device being wound around the forearm RA as illustrated in FIG. 3B. In this state, the adhesion of the adhesive resin material arranged on the electrode arrangement surface 104 maintains a winding state around the forearm RA.

Note that the winding state around the forearm RA only by the adhesion of the resin material is one example. For example, some kind of clip mechanism may be provided at a tip end of the left portion 102 and a tip end of the right portion 103 to hold these portions in an overlapping state.

As described above, the electrical stimulus device of the present embodiment is attached with the sheet-shaped member 100 being wound around the forearm RA, and therefore, can be easily attached. Moreover, the sheet-shaped member 100 is formed in the substantially V-shape. Thus, the user can easily recognize an attachment direction, and can reliably wear the electrical stimulus device in a given direction as illustrated in FIG. 3B.

Note that the example where the electrical stimulus device is attached to the right arm of the user is illustrated in FIGS. 3A and 3B, but the electrical stimulus device may be attached to the left arm.

[3. Internal Circuit Example of Electrical Stimulus Device]

Figure 4:
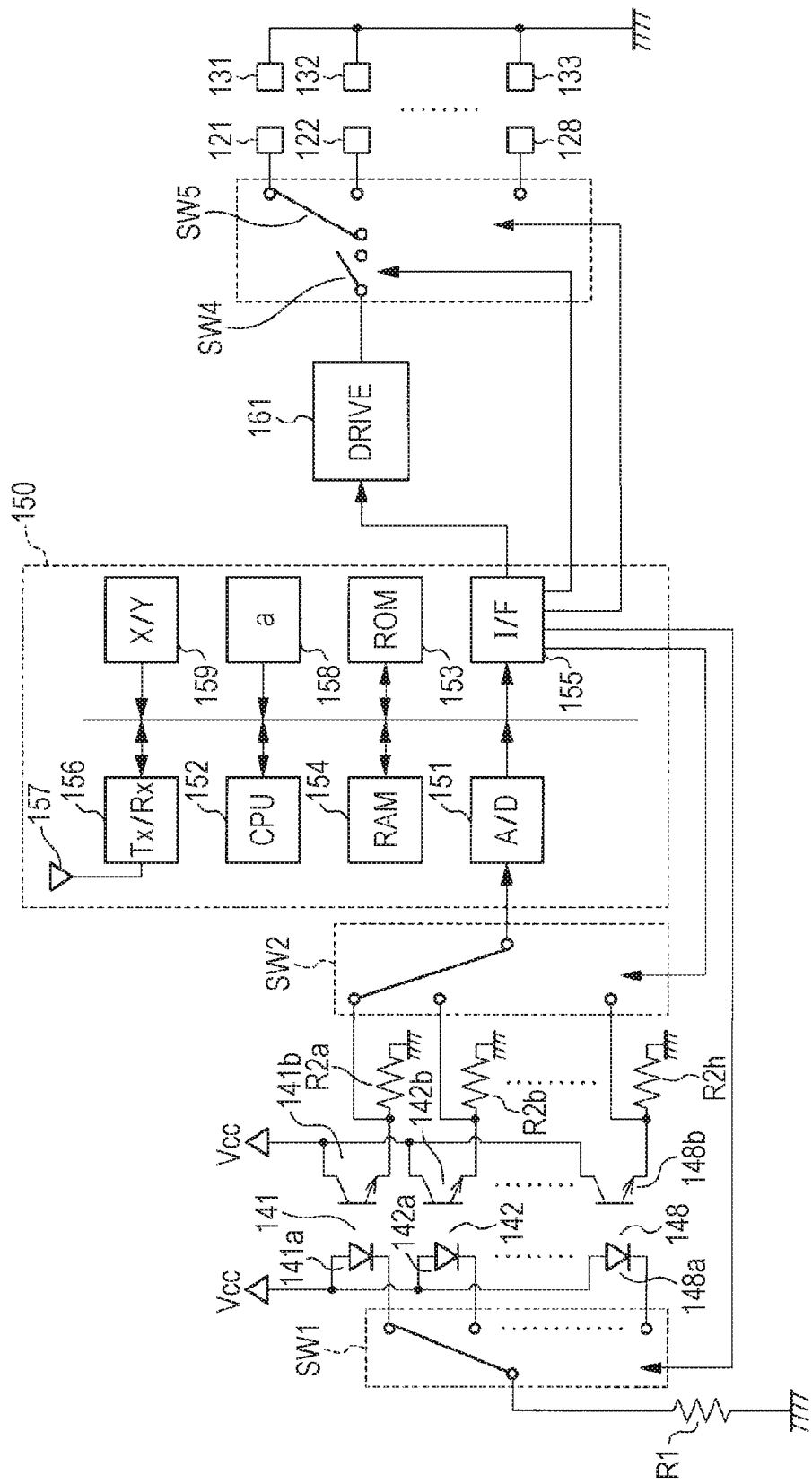
FIG. 4 is a configuration diagram of a circuit example of the electrical stimulus device of an embodiment of the present invention.

FIG. 4 illustrates an internal circuit example of the electrical stimulus device. This circuit is arranged in the circuit housing box 110 illustrated in FIG. 1, for example.

The electrical stimulus device includes the arithmetic processing unit 150, and the arithmetic processing unit 150 generates, based on a command received by the arithmetic processing unit 150 from the outside, the electrical stimulus signal supplied to each electrode. That is, the arithmetic processing unit 150 includes an analog/digital converter 151 configured to capture voltage signals obtained from the optical distance sensors 141 to 148, and a central control unit (CPU) 152 configured to control generation of the electrical stimulus signals. Moreover, the arithmetic processing unit 150 includes a ROM 153 configured to store software etc. necessary for performing control operation by the CPU 152, a RAM 154 configured to hold control data etc., an interface unit 155 configured to output a command from the CPU 152 to each of the electrodes and switches SW1 to SW4, a communication unit 156 configured to perform wireless communication with the outside, an acceleration sensor 158, and an orientation sensor 159. Each of the above-described elements forming the arithmetic processing unit 150 is communicably connected to each other via an internal bus. The communication unit 156 is configured to perform wireless communication with neighboring equipment via the Bluetooth (registered trademark), for example. An antenna 157 is connected to the communication unit 156. The acceleration sensor 158 and the orientation sensor 159 are sensors configured to detect motion and orientation of the arm. A gyroscope sensor or a geomagnetic sensor is applicable as the orientation sensor 159, for example. These sensors included in the arithmetic processing unit 150 are examples, and other sensors may be arranged. Alternatively, it may be configured such that no sensor configured to detect motion or orientation of the arm is arranged.

The arithmetic processing unit 150 performs control of application of the electrical stimulus signals to the electrodes 121 to 128, and performs the processing of determining detection signals of the optical distance sensors 141 to 148.

Each of the optical distance sensors 141 to 148 includes the infrared light emission element 141a to 148a and the infrared light receiving element 141b to 148b. For example, the optical distance sensor 141 includes the infrared light emission element 141a and the infrared light receiving element 141b. The infrared light receiving element 141b detects reflection light of infrared light with which the infrared light emission element 141a irradiates the surface of the forearm of the user, and outputs the detection signal indicating a change in a distance from the optical distance sensor 141 to the surface of the forearm.

DC power Vcc is selectively supplied to the infrared light emission element 141a to 148a. That is, any one (the element 141a in FIG. 4) of the infrared light emission elements is selectively connected to a ground potential side via a resistor R1 by the switch SW1, and the selected infrared light emission element 141a outputs an infrared light signal.

In association with switching of the switch SW1, the switch SW2 configured to select the infrared light receiving element 141b to 148b is also switched. The detection signal obtained by a selected one of the infrared light receiving elements 141b to 148b is supplied to the analog/digital converter 151.

The DC power Vcc is also supplied to each infrared light receiving element 141b to 148b, and the infrared light receiving element 141b to 148b is connected to the ground potential side via a resistor R2a to R2h prepared for each infrared light receiving element 141b to 148b. Then, a detection signal obtained at a connection point between the infrared light receiving element 141b to 148b and the resistor R2a to R2h is supplied to an analog/digital converter 151 side via the switch SW2. Note that the switches SW1, SW2 are switched according to an instruction supplied from the CPU 152 via the interface unit 155.

The detection signal converted into digital data by the analog/digital converter 151 is stored in the RAM 154 under the control of the CPU 152. The data obtained from the optical distance sensors 141 to 148 is used for monitoring whether or not motion of the muscles by means of the electrodes 121 to 128 is accurately made. Such monitoring of motion of the muscles is used in the calibration process of checking a correspondence between each electrode 121 to 128 and the muscle of the forearm of the user when the user wears the electrical stimulus device on the forearm. Moreover, upon later-described actual use as in FIG. 7, monitoring as described above is also used for determining whether or not the hand or the fingers move by application of the electrical stimulus signals.

The electrical stimulus signal application instruction output from the CPU 152 via the interface unit 155 is supplied to a drive circuit 161. The drive circuit 161 is configured to generate an electrical stimulus signal with an instructed voltage, thereby applying the generated electrical stimulus signal to any of the electrodes 121 to 128 selected by the switch SW4 while the switch SW3 is ON. The switch SW3 is a switch for setting a period for applying the electrical stimulus signal, and the switch SW4 is a switch for selecting the electrode 121 to 128 to which the electrical stimulus signal is to be applied. Any of these switches is switched according to the instruction output from the CPU 152 via the interface unit 155.

The ground electrodes 131 to 133, 136, 137 each facing the electrodes 121 to 128 are connected to the ground potential side.

[4. Example of Muscle Stimulated by Each Electrode]

Figure 5:
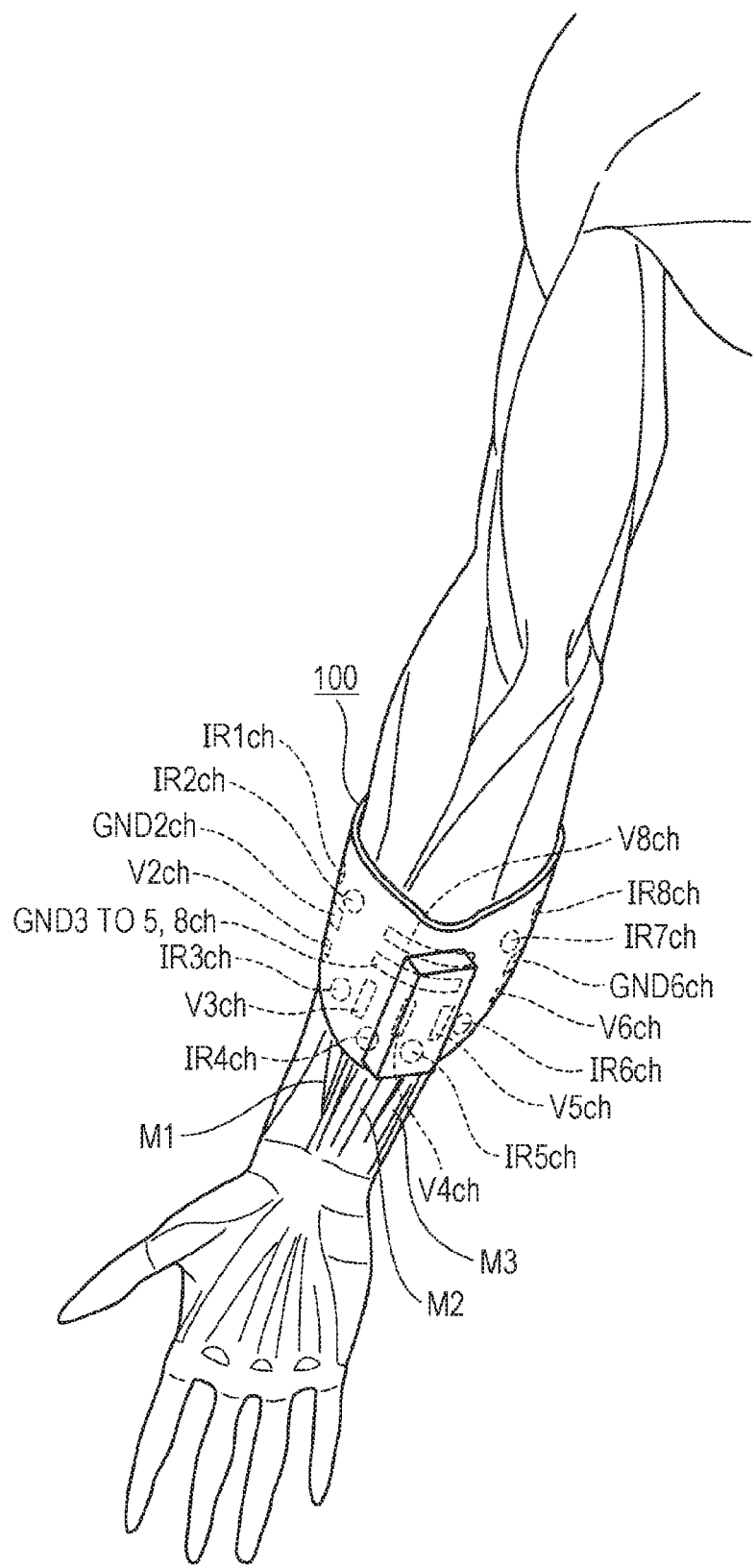
FIG. 5 is a view for describing a relationship (on a right palm side) among the electrical stimulus device of an embodiment of the present invention and arm muscles.
Figure 6:
FIG. 6 is a view for describing the arm muscles in the same state as that of FIG. 5 when the electrical stimulus device is not attached.
Figure 7:
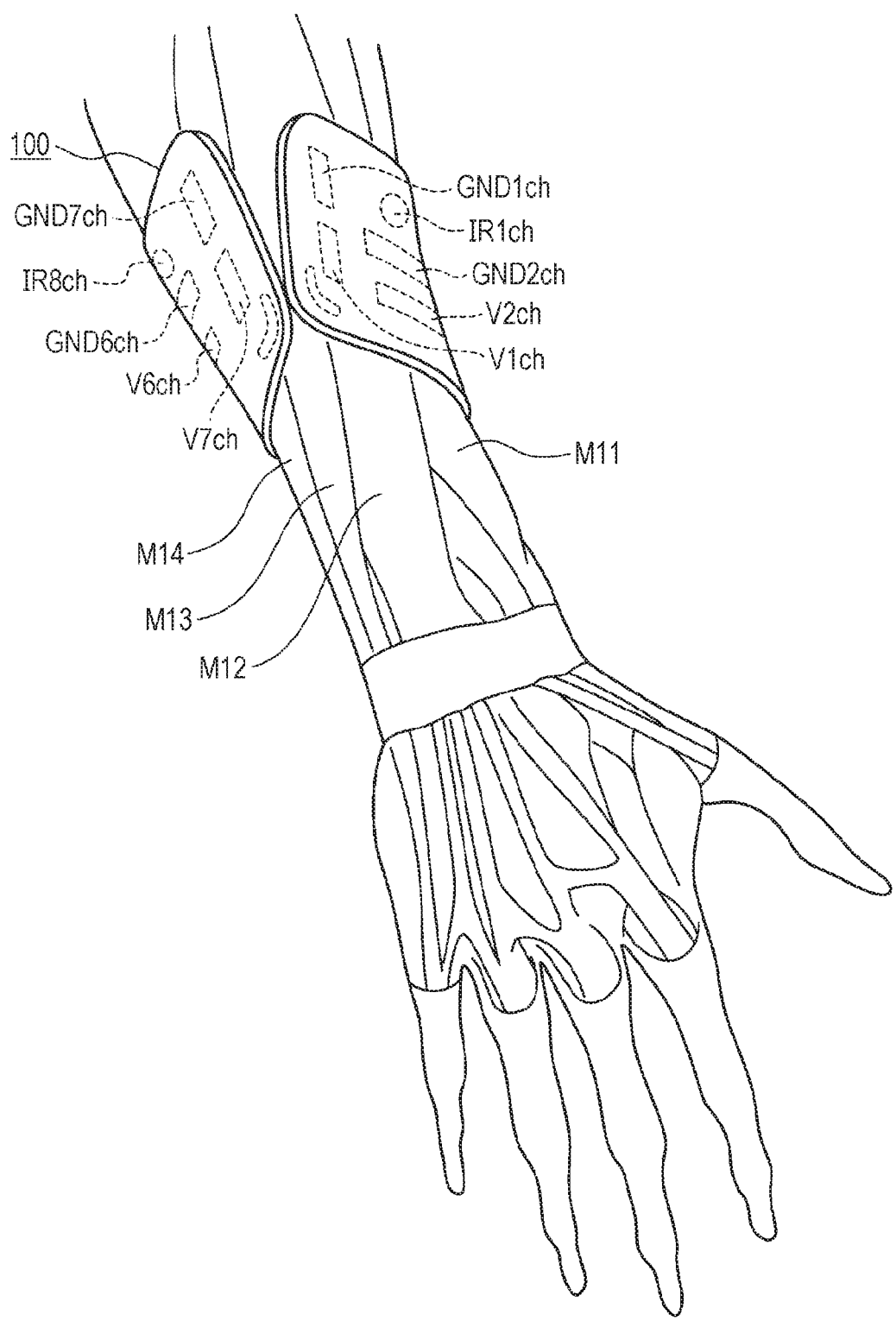
FIG. 7 is a view for describing the relationship (on a right backhand side) among the electrical stimulus device of an embodiment of the present invention and the arm muscles.
Figure 8:
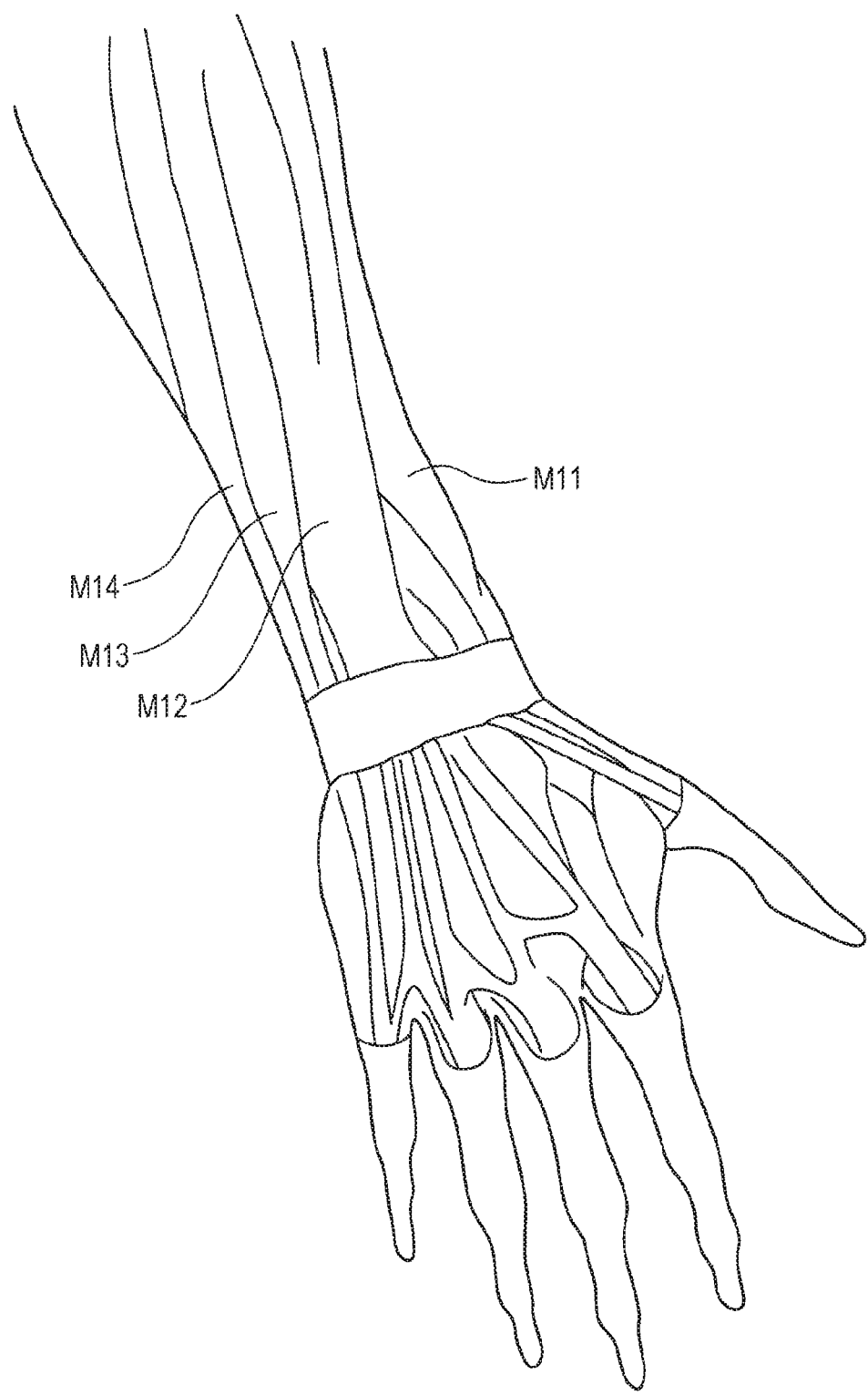
FIG. 8 is a view for describing the arm muscles in the same state as that of FIG. 7 when the electrical stimulus device is not attached.

FIGS. 5 to 8 illustrate examples of the muscles stimulated by the electrodes 121 to 128 arranged on the electrode arrangement surface 104 of the electrical stimulus device. FIG. 5 illustrates the palm-side muscles of the forearm (the right arm) to which the electrical stimulus device is attached, and FIG. 6 illustrates the same arm in a state in which no electrical stimulus device is attached. FIG. 7 illustrates the backhand-side muscles of the forearm (the right arm) to which the electrical stimulus device is attached, and FIG. 8 illustrates the same arm in a state in which no electrical stimulus device is attached.

FIGS. 5 and 7 illustrate an example of a position relationship among each muscle, the electrodes 121 to 128, and the optical distance sensors 141 to 148 when the electrical stimulus device is attached to the forearm such that the center portion 101 of the sheet-shaped member 100 of the electrical stimulus device faces up in a state in which the palm side of the forearm faces up as already described in the attachment example (FIGS. 3A and 3B). Such a relationship is herein illustrated using the channels (V1ch, V2ch, etc.) each assigned to the electrodes.

First, the palm-side muscles of the forearm will be described with reference to FIG. 5. The electrode for V3ch is arranged at a position contacting the flexor carpi radialis muscle M1. The flexor carpi radialis muscle M1 is a muscle for controlling motion for bending the hand or separating the hand from the body axis.

The electrode for V4ch is arranged at a position contacting a muscle M2 connected to the index finger. The electrode for V5ch is arranged at a position contacting a muscle M3 connected to the middle finger. These muscles M2, M3 correspond to the flexor digitorum superficialis muscle of the hand, and are muscles for moving each finger.

Moreover, the electrode for V8ch is arranged at a position contacting all of the muscles M1, M2, M3.

Regarding the optical distance sensors configured to detect motion of the muscles, four optical distance sensors for IR3ch to IR6ch detect motion of the muscles M1, M2, M3.

FIG. 6 illustrates, for reference, the states of the muscles M1, M2, M3 in the state in which no electrical stimulus device is attached.

Next, the backhand-side muscles of the forearm will be described with reference to FIG. 7. The electrode for V2ch is arranged at a position contacting the abductor pollicis longus muscle M11. The abductor pollicis longus muscle M11 is a muscle for controlling motion for extending the thumb or separating the thumb from the hand axis.

The electrode for V1ch is arranged at a position contacting the extensor digitorum muscle M12. The extensor digitorum muscle M12 is for controlling motion for extending other hand fingers than the thumb or extending the hand.

The electrode for V7ch is arranged at a position contacting the extensor digiti minimi muscle M13. The extensor digiti minimi muscle M13 is for controlling motion for extending the little finger.

The electrode for V6ch is arranged at a position contacting the extensor carpi ulnaris muscle M14. The extensor carpi ulnaris muscle M14 is a muscle for controlling motion for bending the hand backward or moving the hand in a body axis direction.

Four optical distance sensors for IR1ch, IR2ch, IR7ch, IR8ch are provided as the optical distance sensors configured to detect motion of the muscles, and detect motion of the muscles M11 to M14.

FIG. 8 illustrates, for reference, the states of the muscles M11 to M14 in the state in which no electrical stimulus device is attached.

Note that the sheet-shaped member 100 of the electrical stimulus device of the present embodiment is in the substantially V-shape. Thus, the center portion electrode arrangement spot 106 at which the electrodes configured to stimulate the palm-side muscles are arranged is positioned at a location close to the wrist as illustrated in FIG. 5, and the right portion electrode arrangement spot 105 and the left portion electrode arrangement spot 107 at which the electrodes configured to stimulate the backhand-side muscles are arranged are positioned at locations apart from the wrist as illustrated in FIG. 7. Thus, advantageous effects are obtained, which allow the optical distance sensors 141 to 148 arranged in the vicinity of the spots 105, 106, 107 to detect motion of each muscle at substantially ideal positions.

Arrangement of the muscles and the electrode 121 to 128 and the optical distance sensor 141 to 148 for each channel as illustrated in FIGS. 5 and 7 has been described by way of example, and each electrode 121 to 128 is not necessarily coincident with a corresponding one of the muscles M1 to M3, M11 to M14. However, in electrode arrangement of the present embodiment, the position of the electrode 121 to 128 and the position of the muscle can be, even with a certain level of individual difference in the muscles of the forearm of the user, coincident with each other at high accuracy.

Specifically, there is a problem that an individual difference in the thicknesses or positions of ones of the muscles of the forearm positioned in a lateral direction as illustrated in FIG. 8, such as the abductor pollicis longus muscle M11 and the extensor carpi ulnaris muscle M14, is extremely great. Specifically, there is the following individual difference: a person with strong muscles has the muscles developed to the vicinity of the tips of the fingers, but a person without strong muscles has the muscles developed only to the vicinity of the elbows.

In typical electrode arrangement, it is difficult to accurately locate a single electrode at a position contacting the muscles M11, M14. On the other hand, in the case of the present embodiment, the elongated rectangular electrodes inclined at the predetermined angles θ1, θ2 are used as the electrodes (V2ch, V6ch) 122, 126 corresponding to the muscles M11, M14, and therefore, the electrodes 122, 126 contact the muscles M11, M14 even with the individual difference. Thus, the muscles M11, M14 can be favorably stimulated. Specifically, it has been confirmed from an experiment that an angle of 32°±5° as the angles θ1, θ2 allows favorable contact of the electrodes 122, 126 with the muscles M11, M14 in various development states. Note that an angle of 32°±5° is one example. Arrangement with inclination at a predetermined angle falling below 90° provides an advantageous effect leading to a favorable state of contact with the muscles positioned in the lateral direction according to the inclination angle.

Even when there is a difference in the thickness or muscle position of the arm of the user targeted for attachment, the electrode 121 to 128 for each channel is substantially accurately arranged at the position corresponding to the muscle M1 to M3, M11 to M14 of the arm of the user. Thus, the electrical stimulus device of the present embodiment can stimulate target muscles without the calibration process of measuring, in advance, a correspondence between the electrode for each channel and the muscle. Moreover, even in the case of performing the calibration process, a relatively-simple calibration process may be only performed to such an extent that it is checked whether or not the target muscles move.

Moreover, the electrical stimulus device of the present embodiment is configured such that the optical distance sensors 141 to 148 are arranged at the periphery of the electrodes, and therefore, motion of the muscles when the electrical stimulus signal is provided from each electrode 121 to 128 of the electrical stimulus device can be directly detected by the optical distance sensors 141 to 148. Thus, the electrical stimulus signals can be provided to the electrodes while motion of the muscles is being monitored. When the above-described calibration process is performed, the detection signals of the optical distance sensors 141 to 148 can be used.

Further, the electrical stimulus device of the present embodiment is configured such that the electrode 128 provided for V8ch and elongated in the circumferential direction of the arm is prepared. Thus, even in a situation where stimulation of the individual muscles by the electrodes 123 to 125 for V3ch to V5ch cannot be performed well, the electrode 128 for V8ch can be used to stimulate the target muscles. That is, the electrical stimulus device of the present embodiment can basically favorably stimulate the target muscles without the need for the precise calibration process as already described above, but a situation where the muscles do not move by stimulation using the electrodes 123 to 125 might occur due to various factors (e.g., sweat of the wearer and displacement during attachment). In this case, the electrode 128 provided for V8ch and elongated in the circumferential direction of the arm is used to stimulate a wide area so that an area including the target muscles can be reliably stimulated. The muscles staying motionless even after stimulation by the electrodes 123 to 125 can be detected from the detection signals of the optical distance sensors 143 to 146 around the electrodes 123 to 125. In this case, the electrode 128 for V8ch may be used.

[5. Use Example of Electrical Stimulus Device]

Figure 9:
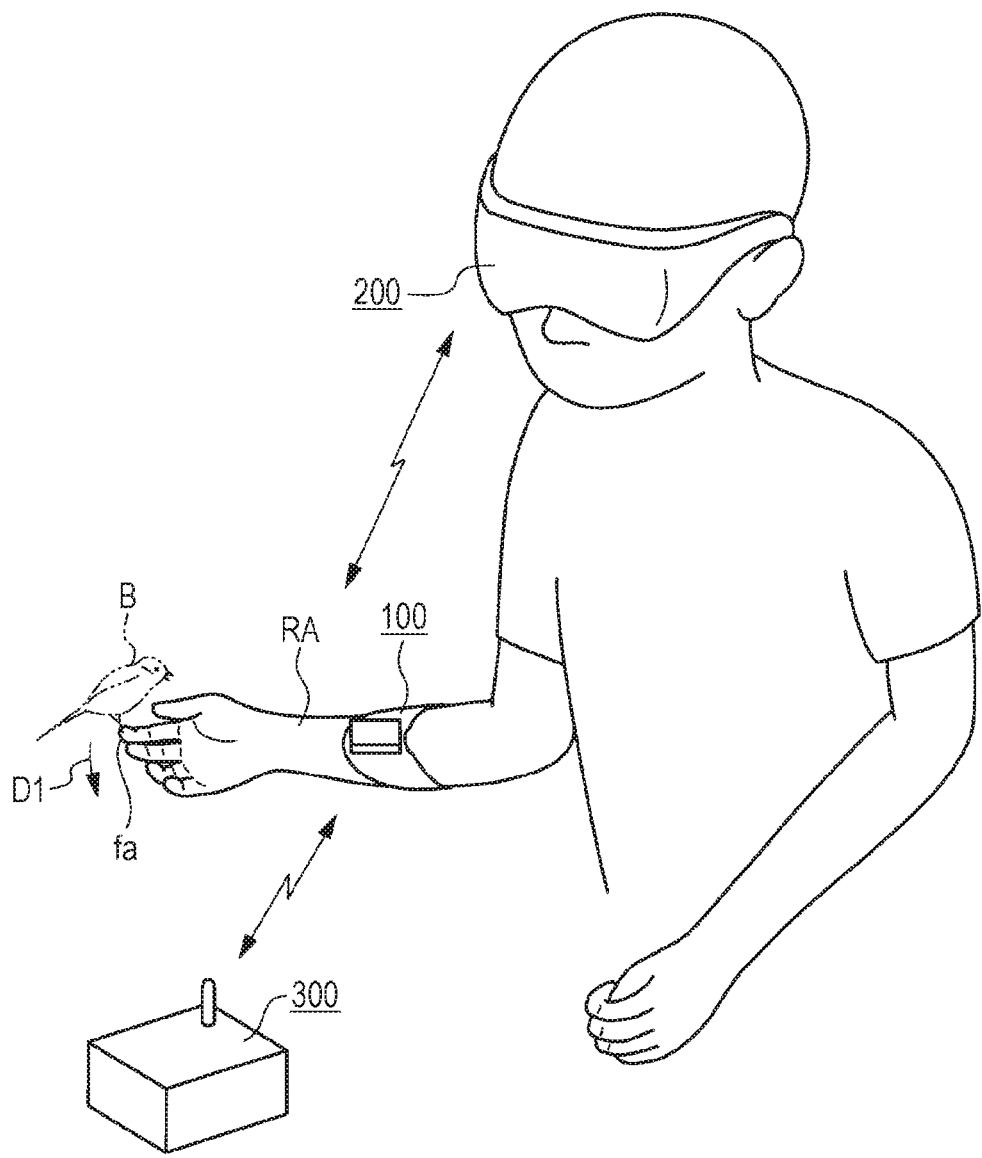
FIG. 9 is a view for describing a use example of the electrical stimulus device of an embodiment of the present invention.

FIG. 9 illustrates a use example of the electrical stimulus device of the present embodiment.

In the example of FIG. 9, the electrical stimulus device is attached to the forearm RA of the right arm of the user. Further, the user wears a head mount display 200, and a virtual video wirelessly transferred from a virtual video reproduction device 300 is displayed by the head mount display 200.

Moreover, the virtual video reproduction device 300 is configured to instruct, in association with displaying of the video by the head mount display 200, the timing of generating an electrical stimulus signal to be provided to a specific muscle of the forearm RA from the electrical stimulus device.

For example, as illustrated in FIG. 9, the head mount display 200 displays a video of a little bird B on a finger of the right hand of the user. In this state, according to the instruction from the virtual video reproduction device 300, the electrical stimulus device applies, to the forearm RA, an electrical stimulus signal from a specific electrode of the electrodes 121 to 128 arranged on the sheet-shaped member 100. The specific electrode configured to apply the electrical stimulus signal in this case is an electrode configured to stimulate the muscle for moving the finger f1 as if the user sees the little bird B on the finger f1.

Application of the electrical stimulus signal leads to downward motion D1 of the finger f1. The motion D1 is performed by application of the electrical stimulus signal, and therefore, is independent of user's intention. Thus, the user is under impression that the finger f1 is moved due to the weight of the little bird B, and therefore, can feel immersed in the virtual video provided by the head mount display 200.

Moreover, when the little bird B displayed as the video flies out of the finger f1, the finger f1 is moved in the opposite direction (upward) of the motion D1, and therefore, the user feels, by a sense of the finger f1, as if the little bird flew out.

FIG. 9 illustrates motion of the single finger f1, but motion of the fingers or hand can be realized according to the function of each muscle by application of the electrical stimulus signal to each muscle described with reference to FIGS. 5 and 7.

[6. Example of Application to Band Member]

In the example of FIG. 1, the substantially V-shaped sheet-shaped member 100 is attached to the arm of the user with the sheet-shaped member 100 being wound around the arm. However, a member in a shape different from that of the sheet-shaped member 100 may be wound around the arm.

Figure 10:
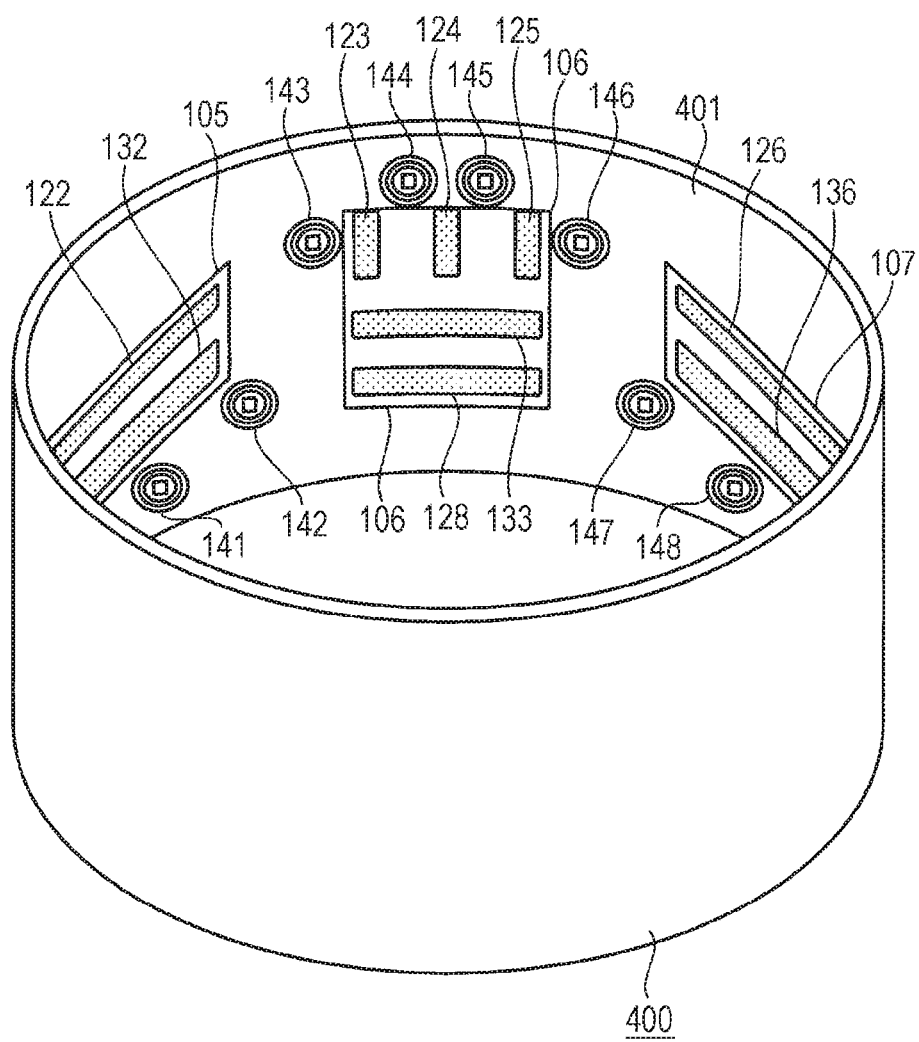
FIG. 10 is a view for describing an example where the electrical stimulus device of an embodiment of the present invention is applied to a band member.
Figure 11:
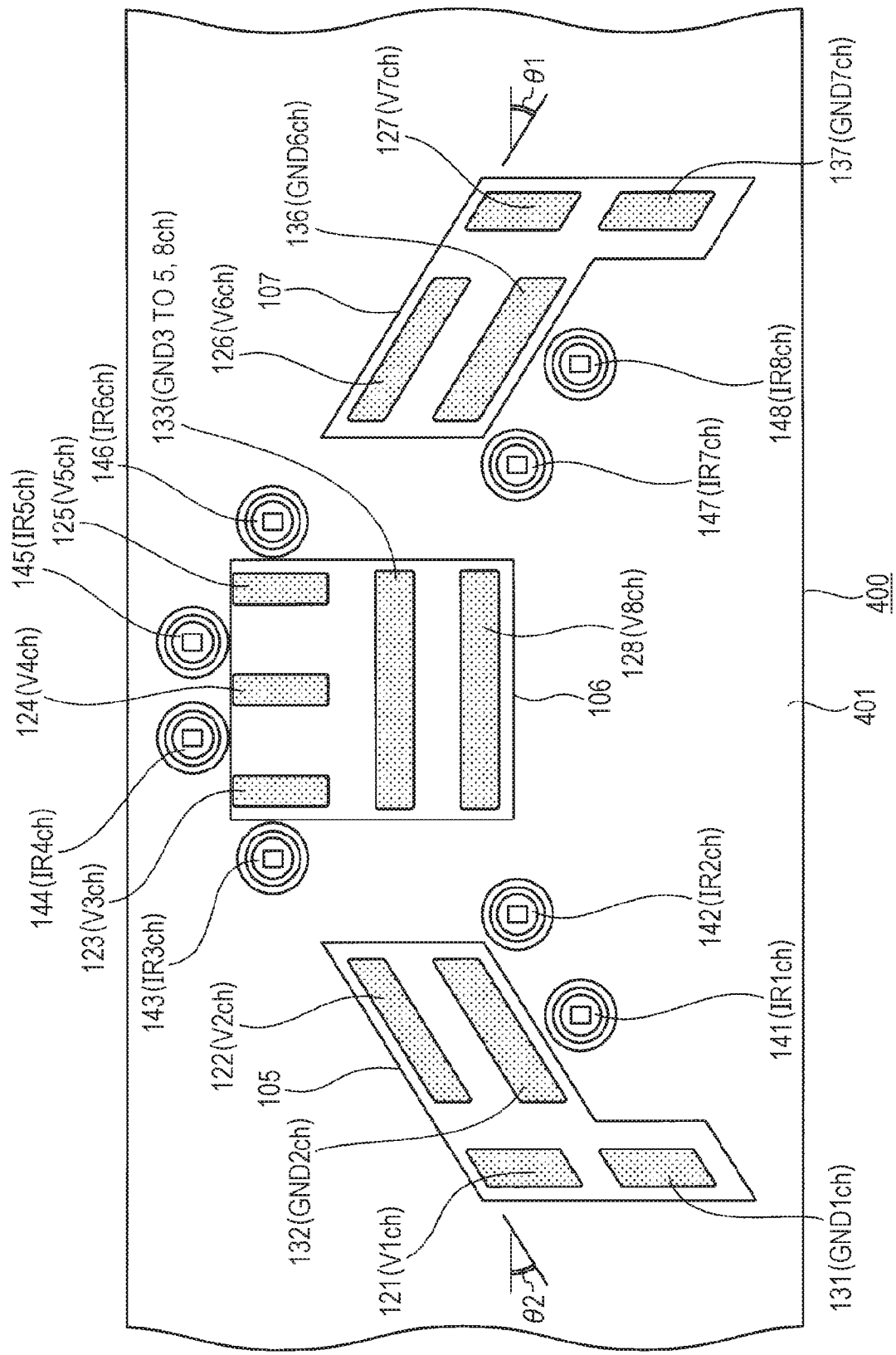
FIG. 11 is a plan view of a state when the band member of FIG. 10 is opened up.

FIGS. 10 and 11 illustrate an example where the electrodes are arranged on a band-shaped member 400 formed in an annular shape.

In the example of FIG. 10, the annular band-shaped member 400 is prepared, and the electrodes 121 to 128, the ground electrodes 131 to 133, 136, 137, and the optical distance sensors 141 to 148 are arranged on an inner surface 401 of the band-shaped member 400.

An arrangement state of the electrodes 121 to 128, 131 to 133, 136, 137 and the optical distance sensors 141 to 148 is substantially the same as electrode arrangement of the sheet-shaped member 100 illustrated in FIG. 2. That is, as illustrated in FIG. 11 with the inner surface 401 of the band-shaped member 400 being opened up, the right portion electrode arrangement spot 105, the center portion electrode arrangement spot 106, and the left portion electrode arrangement spot 107 are arranged on the inner surface 401, and each electrode 121 to 128, 131 to 133, 136, 137 is arranged as in the example of FIG. 2 in a corresponding one of the arrangement spots 105 to 107. Further, the optical distance sensors 141 to 148 are arranged at the periphery of the arrangement spots 105 to 107.

As in θ1, θ2 illustrated in FIG. 2, the inclination angles θ1, θ2 of the diagonally-inclined electrodes 122, 132, 126, 136 at the right portion electrode arrangement spot 105 and the left portion electrode arrangement spot 107 are preferably an angle of 32°±5°.

In the case of the electrical stimulus device using the band-shaped member 400 illustrated in FIGS. 10 and 11, advantageous effects similar to those of the electrical stimulus device of the example of FIG. 1 are also obtained.

[7. Other Variations]

Note that the electrical stimulus devices of the above-described example embodiments are preferable examples, and modifications/changes can be made without departing from the gist of the present invention.

For example, in the example of FIG. 1, the sheet-shaped member 100 and the circuit housing box 110 are configured integrally. On the other hand, the sheet-shaped member 100 and the circuit housing box 110 may be configured detachably, and the sheet-shaped member 100 may be replaced when the resin material arranged on the sheet-shaped member 100 and exhibiting the adhesion is deteriorated.

Arrangement of the circuit housing box 110 at the center of the surface of the sheet-shaped member 100 as in the example of FIG. 1 is also an example, and the circuit housing box 110 may be attached to other spots.

Electrode arrangement of the example of FIG. 2 or FIG. 10 is arrangement for performing motion of all fingers of the hand or motion of the entirety of the hand. For example, in the case of requesting specific motion such as motion of a single specific finger or motion of the entirety of the hand, any one of the electrodes or a limited number of electrodes may be arranged.

In electrode arrangement of the example of FIG. 2, the electrode 128 for V8ch is the backup electrode, and is also the electrode used in a case where the fingers etc. are not moved by the electrodes 123 to 125 for V3ch to V5ch. Thus, depending on the type of usage, it may be configured such that the electrode 128 for V8ch is not arranged.

Moreover, in the above-described examples of FIGS. 1 and 2, the sheet-shaped member 100 of the electrical stimulus device is in the substantially V-shape. However, as described in the example of FIG. 10, the electrode arrangement member itself is not necessarily in the V-shape. As long as the specific electrodes 122, 126 and the specific ground electrodes 132, 136 are relatively-long band-shaped electrodes in an inclined state as illustrated in FIG. 2, the advantageous effect of stimulating the target muscles even with the individual user difference as described above is obtained. In FIG. 10 described above, one example of the shape other than the V-shape is illustrated. However, the electrode arrangement member may be in a shape different from those of the illustrated examples.

Note that when the sheet-shaped member 100 is in the substantially V-shape as illustrated in FIG. 1, there is an advantageous effect that the attachment direction is easily recognizable upon attachment to the forearm, and a shape from which a front-to-back direction is easily recognizable, such as the V-shape, is preferable.

In the above-described example embodiments, the infrared light sensors are used as the optical distance sensors 141 to 148, but distance sensors employing other techniques may be used to detection motion of the muscles.

In the circuit example illustrated in FIG. 4, the electrical stimulus device includes the built-in communication unit 156 to wirelessly receive the instruction from the outside, but may receive, from external equipment connected via a cable, the instruction for moving the muscles. Alternatively, the electrical stimulus device itself may determine a surrounding situation to apply an electrical stimulus signal.

DESCRIPTION OF REFERENCE SIGNS 100 sheet-shaped member
101 center portion
101a upper side of center portion
102 left portion
103 right portion
104 electrode arrangement surface
105 right portion electrode arrangement spot
106 center portion electrode arrangement spot
107 left portion electrode arrangement spot
110 circuit housing box
111 connection terminal
121 to 128 electrode
131 to 133, 136, 137 ground electrode
141 to 148 optical distance sensor
150 arithmetic processing unit
151 analog/digital converter
152 central processing unit (CPU)
153 ROM
154 RAM
155 interface unit
156 communication unit
157 antenna
158 acceleration sensor
159 orientation sensor
161 drive circuit
200 head mount display
300 virtual video reproduction device
400 band-shaped member
401 inner surface

The invention claimed is:

1. An electrical stimulus device comprising:
a sheet-shaped member configured to be wound around a forearm of a user including a muscle displaceable in response to an electrical stimulus signal;
multiple electrodes arranged on one surface of the sheet-shaped member;
multiple optical distance sensors arranged on the one surface of the sheet-shaped member; and
an electrical stimulus generation circuit located on other surface of the sheet-shaped member and configured to generate the electrical stimulus signal,
wherein the multiple electrodes are configured to output the electrical stimulus signal generated by the electrical stimulus generation circuit,
the multiple electrodes comprises at least one specific electrode arranged on the one surface of the sheet-shaped member such that the specific electrode is configured to provide the electrical stimulus signal to a specific muscle of the forearm at a position facing the specific electrode,
at least one of the multiple optical distance sensors is configured to detect displacement of the specific muscle of the forearm,
the at least one specific electrode is a substantially rectangular electrode arranged with the substantially rectangular electrode being inclined with respect to a circumferential direction of the forearm of the user upon winding of the sheet-shaped member around the forearm at a first predetermined angle of lower than 90°, and
each of a right portion and a left portion of the sheet-shaped member is respectively inclined with respect to the circumferential direction in a second predetermined amount of angle.

2. The electrical stimulus device according to claim 1, wherein
the multiple electrodes are separately arranged at at least three locations including a center portion electrode arrangement spot at a specific position of the sheet-shaped member, a left portion electrode arrangement spot on a left side of the specific position in the circumferential direction, and a right portion electrode arrangement spot on a right side of the specific position in the circumferential direction, and
the at least one specific electrode includes at least one electrode arranged at the left portion electrode arrangement spot and at least one electrode arranged at the right portion electrode arrangement spot, which are substantially rectangular electrodes arranged with the substantially rectangular electrodes being inclined in opposite directions at the first predetermined angle.

3. The electrical stimulus device according to claim 2, wherein the first predetermined angle is set to 32°±5°.

4. The electrical stimulus device according to claim 2, wherein at least one electrode arranged at a center portion of the sheet-shaped member is an electrode extending in the circumferential direction of the forearm of the user.

5. The electrical stimulus device according to claim 1, wherein the sheet-shaped member has a substantially V-shape.

6. The electrical stimulus device according to claim 1, wherein the sheet-shaped member has a substantially V-shape comprising the left portion and the right portion inclined in opposite directions at the second predetermined amount of angle.

7. The electrical stimulus device according to claim 6, wherein the second predetermined amount of angle is set to approximately 32°.

8. The electrical stimulus device according to claim 1, wherein the at least one of the multiple optical distance sensors is configured to detect a change in a distance from a sensor arrangement surface on which the at least one of the multiple optical distance sensors is arranged to a surface of the specific muscle of the forearm.

9. The electrical stimulus device according to claim 1, wherein the at least one of the multiple optical distance sensors is configured to detect a motion of the specific muscle of the forearm.

10. The electrical stimulus device according to claim 1, wherein the substantially rectangular electrode is arranged on the one surface of the sheet-shaped member at a position contacting either one of an abductor pollicis longus muscle or an extensor carpi ulnaris muscle upon winding of the sheet-shaped member around the forearm.

11. The electrical stimulus device according to claim 1, wherein the amounts of the first and second predetermined angles are substantially the same with each other.

* * * * *